United States Patent
Wise et al.

(10) Patent No.: US 6,595,972 B1
(45) Date of Patent: Jul. 22, 2003

(54) WEARABLE ARTICLE HAVING A SPACER MAINTAINING A VOID SPACE

(75) Inventors: Brandon E. Wise, Cincinnati, OH (US); Kimberly A. Dreier, Cincinnati, OH (US); Donald C. Roe, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/579,904

(22) Filed: May 26, 2000

(51) Int. Cl.⁷ .............................................. A61F 13/15
(52) U.S. Cl. ........................ 604/385.01; 604/385.101
(58) Field of Search ..................... 604/385.01, 358, 604/378, 385.101, 385.23

(56) References Cited

U.S. PATENT DOCUMENTS

| | | | |
|---|---|---|---|
| 3,860,003 A | 1/1975 | Buell | 128/287 |
| 4,078,568 A | 3/1978 | Etes et al. | 128/283 |
| 4,140,115 A | 2/1979 | Schonfeld | 128/156 |
| 4,192,785 A | 3/1980 | Chen et al. | 260/17.4 GC |
| 4,231,369 A | 11/1980 | Sorensen et al. | 128/283 |
| 4,393,080 A | 7/1983 | Pawelchak et al. | 428/355 |
| 4,505,976 A | 3/1985 | Doehnert et al. | 428/355 |
| 4,551,490 A | 11/1985 | Doyle et al. | 524/22 |
| 4,593,053 A | 6/1986 | Jevne et al. | 523/111 |
| 4,699,146 A | 10/1987 | Sieverding | 128/640 |
| 4,731,065 A * | 3/1988 | Yamada | 604/385.1 |
| 4,738,257 A | 4/1988 | Meyer et al. | 128/156 |
| 4,768,503 A | 9/1988 | Highgate et al. | 128/156 |
| 4,892,536 A | 1/1990 | DesMarais et al. | 604/385.2 |
| 4,968,312 A | 11/1990 | Khan | 604/388.1 |
| 4,990,147 A | 2/1991 | Freeland | 604/385.2 |
| 5,037,416 A | 8/1991 | Allen et al. | 604/385.1 |
| 5,062,840 A | 11/1991 | Holt et al. | 604/385.1 |
| 5,151,092 A | 9/1992 | Buell et al. | 604/385.2 |
| 5,171,236 A | 12/1992 | Dreier et al. | 604/369 |
| 5,269,755 A | 12/1993 | Bodicky | 604/53 |
| 5,306,266 A | 4/1994 | Freeland | 604/385.1 |
| 5,330,459 A * | 7/1994 | Lavon et al. | 604/385.1 |
| 5,397,318 A | 3/1995 | Dreier | 604/385.2 |
| 5,514,121 A | 5/1996 | Roe et al. | 604/385.1 |
| 5,540,671 A | 7/1996 | Dreier | 604/385.2 |
| 5,554,142 A | 9/1996 | Dreier et al. | 604/385.1 |
| 5,625,222 A | 4/1997 | Yoneda et al. | 257/687 |
| 5,643,241 A * | 7/1997 | Ahr et al. | 604/385.1 |
| 5,652,194 A * | 7/1997 | Dyer et al. | 502/402 |
| 5,653,703 A | 8/1997 | Roe et al. | 604/385.1 |
| 5,726,250 A | 3/1998 | Zajaczkowski | 525/296 |
| 5,873,870 A | 2/1999 | Seitz et al. | 604/385.1 |
| 5,897,545 A | 4/1999 | Kline et al. | 604/386 |
| 5,904,673 A | 5/1999 | Roe et al. | 604/385.2 |
| 5,931,827 A | 8/1999 | Buell et al. | 604/385.2 |
| 5,941,864 A | 8/1999 | Roe | 604/378 |
| 5,977,430 A | 11/1999 | Roe et al. | 604/378 |
| 5,997,520 A | 12/1999 | Ahr et al. | 604/385.1 |
| 6,004,306 A | 12/1999 | Robles et al. | 604/385.1 |
| 6,010,491 A | 1/2000 | Roe et al. | 604/385.1 |
| 6,013,063 A | 1/2000 | Roe et al. | 604/385.1 |
| 6,133,501 A * | 10/2000 | Hallock et al. | 604/369 |
| 6,180,847 B1 * | 1/2001 | Ahr et al. | 604/367 |
| 6,186,991 B1 * | 2/2001 | Roe et al. | 604/361 |
| 6,280,426 B1 * | 8/2001 | Turner et al. | 604/385.01 |

FOREIGN PATENT DOCUMENTS

| | | | |
|---|---|---|---|
| FR | 002561078 A1 * | 9/1985 | A61F/5/44 |
| WO | WO 93/25172 | 12/1993 | A61F/13/15 |
| WO | WO 94/13235 A1 | 6/1994 | A61F/13/00 |
| WO | WO 94/14395 | 7/1994 | A61F/13/15 |
| WO | WO 98 08476 | 3/1998 | |
| WO | WO 00/24350 | 5/2000 | |

* cited by examiner

*Primary Examiner*—Weilun Lo
*Assistant Examiner*—Jacqueline Stephens
(74) *Attorney, Agent, or Firm*—Jeffrey R. Moore; Jay A. Krebs; Ken K. Patel

(57) ABSTRACT

An absorbent article having a void space for receiving bodily exudates comprises a spacer including an opening in communication with the void space and a body for maintaining at least a portion of the void space. The spacer includes an alignment guide which aids in keeping the spacer opening in a desired configuration for receiving and containing bodily exudates.

10 Claims, 6 Drawing Sheets

US 6,595,972 B1

WEARABLE ARTICLE HAVING A SPACER MAINTAINING A VOID SPACE

FIELD OF THE INVENTION

This invention is directed to hygienic absorbent articles, such as diapers, adult incontinence articles, feminine protection articles and the like.

BACKGROUND OF THE INVENTION

Absorbent articles are well known in the art. These articles typically have an absorbent core, which is held or positioned against the body of the wearer during use by a fastening system, such that the bodily exudates are caught by the article. Typical absorbent articles include a topsheet facing the wearer which permits fluid exudates to pass through and a backsheet which prevents the exudates from escaping from the absorbent article.

Many advancements have been made in the art since the introduction of the disposable absorbent article. However, problems still exist relating to the acceptance and storage of feces, and especially runny and pasty feces. The problem has been difficult to resolve because feces generally will not pass through a topsheet and thus, remains free to move about in the diaper until the diaper is changed. This often leads to feces escaping the diaper or soiling of the wearer's skin.

In order to prevent the feces from escaping the diaper or soiling the skin, apertures have been provided in the topsheet which allow the feces to pass to the absorbent core. In addition, spacers have been provided to maintain a void space in the diaper for receiving the feces. However, the aperture/spacer combinations are difficult to position during application of the diaper and often move from the desired position when the diaper is worn.

Thus, it would be desirable to provide absorbent articles with improved fit and alignment capability which can be sustained during use. It would also be desirable to provide an article which can maintain a desired configuration for accepting and storing bodily exudates, especially feces, during use. Further, it would be advantageous to provide such an article with a topical or body adhesive which helps maintain the article in the desired configuration (e.g., the aperture is aligned with the anus) without irritating or harming the wearer's skin.

SUMMARY OF THE INVENTION

In order to solve one or more of the problems found in the art, an absorbent article, such as an adult incontinence article, baby diaper or feminine hygiene pad, having a void space maintained by a spacer is provided having an alignment guide which aids in keeping an opening in the spacer in a desired configuration for receiving and storing bodily exudates.

Preferably, the absorbent article comprises a topsheet including an aperture in communication with a void space for receiving fecal waste therein, a backsheet joined with at least a portion of the topsheet, and an absorbent core disposed between at least a portion of the topsheet and the backsheet. A spacer is disposed between the topsheet and the backsheet with an opening defining a passageway between the aperture and the void space. The opening also provides at least a portion of the void space which is maintained under applied pressures generated by the wearer. An alignment guide extends from the spacer, between a wearer's legs holding the spacer in the correct longitudinal and lateral position in order to maintain the opening in the correct Z-direction orientation with the wearer's anus.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIG. 5b is a cross sectional view of the spacer depicted in FIG. 5a.

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and study of the included drawings.

DEFINITIONS

As used herein, the following terms have the following meanings:

"Absorbent article" refers to devices which absorb and contain liquid, and more specifically, refers to devices which are placed against or in proximity to the body of the wearer to absorb and contain the various exudates discharged from the body.

"Longitudinal" is a direction running parallel to the maximum linear dimension of the article and includes directions within ±45° of the longitudinal direction.

The "lateral" or "transverse" direction is orthogonal to the longitudinal direction.

The "Z-direction" is orthogonal to both the longitudinal and transverse directions.

The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

A "unitary" absorbent article refers to absorbent articles which are formed of separate parts united together to form a coordinated entity so that they do not require separate manipulative parts like a separate holder and liner.

As used herein, the term "diaper" refers to an absorbent article generally worn by infants and incontinent persons about the lower torso.

As used herein, the term "void space" is a cavity sized to accept bodily exudates such as fecal material.

The present invention provides an absorbent article having a spacer which maintains an opening for receiving bodily exudates therein in proximity with a point of discharge on a wearer through use of an alignment guide. The spacer is equally applicable to absorbent articles such as incontinence briefs, incontinence undergarments, absorbent inserts, diaper holders and liners, feminine hygiene garments, bandages and the like, however, a preferred embodiment of an absorbent article of the present invention is a unitary disposable absorbent article, such as the disposable diaper 20, shown in FIG. 1.

Figure 1:
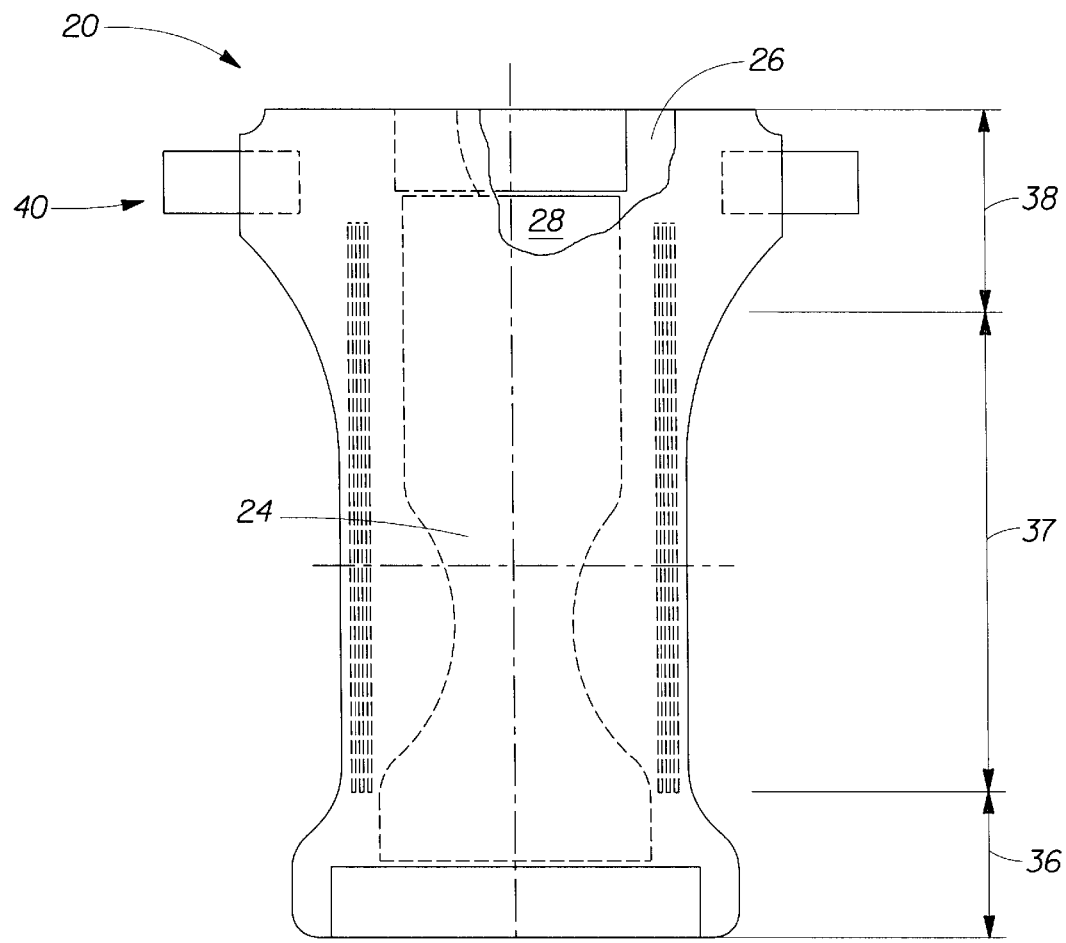
FIG. 1 is a plan view of a disposable diaper.

FIG. 1 is a plan view of the diaper 20 in its flat out, uncontracted state (i.e., without elastic induced contraction) with portions of the structure being cut away to more clearly show the underlying structure of the diaper 20 and with the portion of the diaper 20 which contacts the wearer facing the viewer. One end portion 36 of the diaper 20 is configured as a first waist region of the diaper 20. The opposite end portion 38 is configured as a second waist region of the diaper 20. An intermediate portion 37 of the diaper 20 is configured as a crotch region which extends longitudinally between the first and second waist regions 36 and 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The diaper 20 preferably comprises a liquid pervious topsheet 24, a liquid impervious backsheet 26, and an absorbent core 28 encased between the topsheet 24 and the backsheet 26. The topsheet 24 may be fully or partially elasticated or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which is incorporated by reference herein.

The diaper 20 preferably also includes a fastener such as a hook and loop type fastening system 40 including at least one engaging component (male fastening component) and at least one landing zone (female fastening component). The diaper 20 may also include such other features as are known in the art including leg cuffs, front and rear ear panels, waist cap features, elastics and the like to provide better fit, containment and aesthetic characteristics. Such additional features are well known in the art and are described in U.S. Pat. No. 3,860,003; and U.S. Pat. No. 5,151,092 which are incorporated by reference herein.

In addition, the present invention may be suitable for other diaper embodiments including those disclosed in U.S. Pat. No. 6,010,491 titled "Viscous Fluid Bodily Waste Management Article" issued Jan. 4, 2000; U.S. Pat. No. 5,873,870 titled "Fit And Sustained Fit Of A Diaper Via Chassis And Core Modifications" issued Feb. 23, 1999; U.S. Pat. No. 5,897,545 titled "Elastomeric Side Panel for Use with Convertible Absorbent Articles" issued Apr. 27, 1999; U.S. Pat. No. 5,904,673 titled "Absorbent Article With Structural Elastic-Like Film Web Waist Belt" issued May 18, 1999; U.S. Pat. No. 5,931,827 titled "Disposable Pull On Pant" issued Aug. 3, 1999; U.S. Pat. No. 5,977,430 titled "Absorbent Article With Macro-Particulate Storage Structure" issued Nov. 2, 1999 and U.S. Pat. No. 6,004,306 titled "Absorbent Article With Multi-Directional Extensible Side Panels" issued Dec. 21, 1999, the disclosures of which are incorporated herein by reference.

Preferred embodiments of the present invention are particularly suited to the entrapment or encapsulation of bodily waste and thus reduce the amount and area of contamination of the wearer's skin by the waste. In addition to spacers, other embodiments of the present invention for limiting the movement of waste and/or providing the containment thereof may include pockets for receiving and containing waste, barriers for limiting the movement of waste in the article, compartments or voids which accept and contain waste materials deposited in the diaper 20, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al. on Dec. 15, 1992 entitled "Disposable Absorbent Article Having Core Spacers"; U.S. Patent No. 5,397,318 issued to Dreier on Mar. 14, 1995 entitled "Absorbent Article Having A Pocket Cuff"; U.S. Pat. No. 5,540,671 issued to Dreier on Jul. 30, 1996 entitled "Absorbent Article Having A Pocket Cuff With An Apex"; PCT Application WO 93/25172 published Dec. 3, 1993 entitled "Spacers For Use In Hygienic Absorbent Articles And Disposable Absorbent Articles Having Such Spacer"; U.S. Pat. No. 5,306,266 entitled "Flexible Spacers For Use In Disposable Absorbent Articles" issued to Freeland on Apr. 26, 1994; and U.S. Pat. No. 5,997,520 entitled "Disposable Absorbent Article With Selectively Expandable or Inflatable Component"issued to Ahr et al. on Dec. 7, 1999. Examples of compartments or voids are disclosed in U.S. Pat. No. 4,968,312 entitled "Disposable Fecal Compartmenting Diaper" issued to Khan on Nov. 6, 1990; U.S. Pat. No. 4,990,147 entitled "Absorbent Article With Elastic Liner For Waste Material Isolation" issued to Freeland on Feb. 5, 1991; U.S. Pat. No. 5,62,840, entitled "Disposable Diapers" issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets" issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Pat. No. WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition issued Aug. 5, 1997 to Roe, et al. Examples of other structures especially suitable for management of low viscosity feces are disclosed in U.S. Pat. Nos. 5,941,864 issued to Roe et al. on Aug. 24, 1999; U.S. Pat. No. 5,977,430 issued to Roe et al. on Nov. 2, 1999 and 6,013,063 issued to Roe et al. on Jan. 11, 2000. All of the above-cited references are hereby incorporated by reference herein.

In order to achieve the desired level of entrapment or encapsulation of bodily waste, especially for viscous bodily waste such as feces, at least two functions should be performed. First, the diaper should provide a void space for the waste which is at least partially maintained even under applied pressures which are typical of those generated by a wearer on the crotch region of the article while the wearer is in a seated position. Second, the diaper should have means for maintaining a passageway between the void space and a waste exit point (e.g., anus) on the wearer.

Figure 2A:
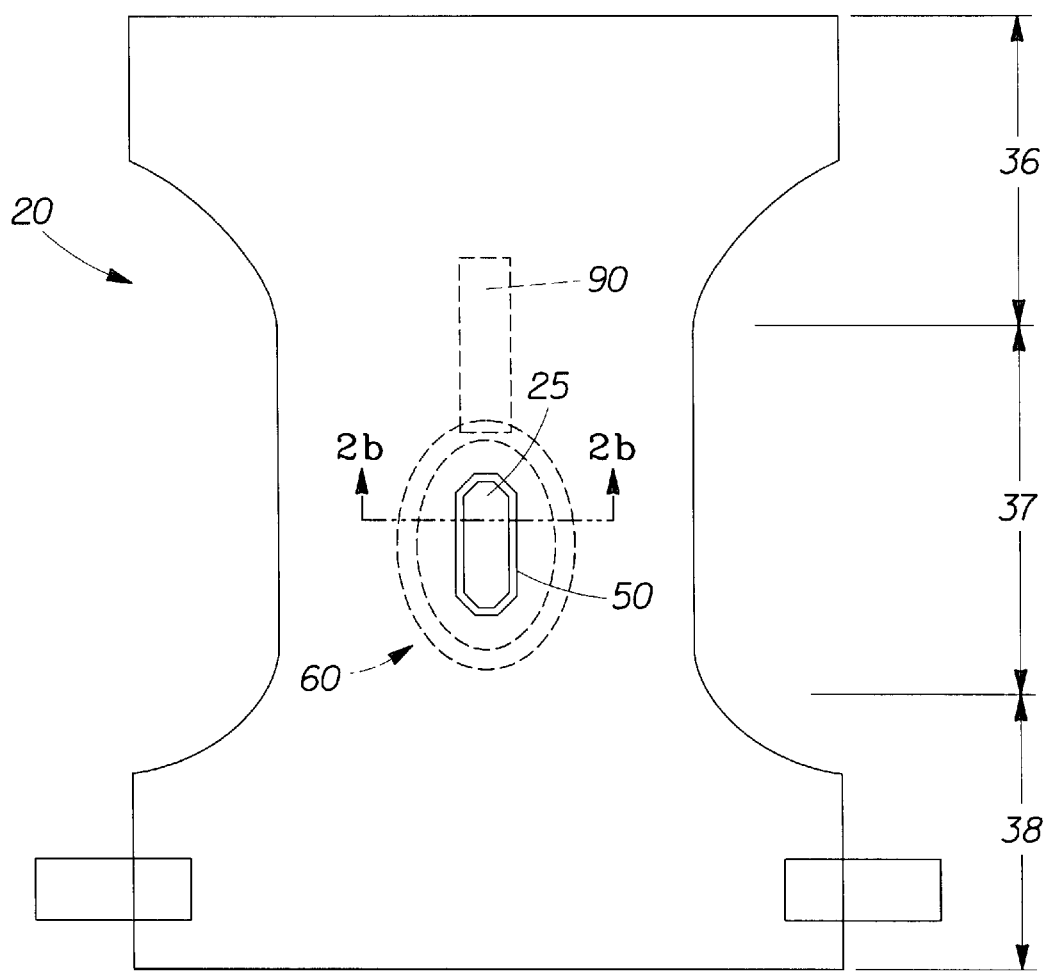
FIG. 2a is a plan view of a disposable diaper configuration of the present invention.
Figure 2B:
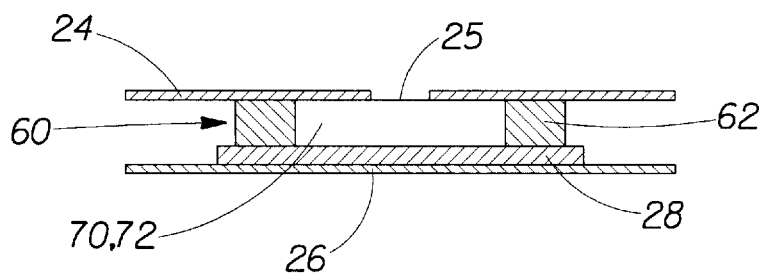
FIG. 2b is a cross-sectional view of the embodiment depicted in FIG. 2a showing the spacer opening providing the void space.

In order to provide a void space which can be at least partially maintained under pressure, preferred embodiments of the present invention include one or more spacers 60. As shown in FIGS. 2a and 2b, the spacer 60 is intended to space the topsheet 24 or other covering layer away from the absorbent core 28 and/or other underlying layers such as sublayers, acquisition layers and the like in order to provide a void space for entrapping or encapsulating bodily waste. It is also contemplated that the spacer 60 may space apart any other two elements of the diaper 20, including but not limited to the topsheet 24 and the backsheet 26, the acquisition layer and the core 28, the core 28 and the backsheet 26, etc.

The spacer 60 generally includes a body 62 defining an opening 70 providing either all or a portion of a void space for entrapping or encapsulating bodily waste. For the embodiment shown in FIGS. 2a and 2b, the opening 70 is in register with an aperture 25 in the topsheet 24. The opening 70 creates a void space 72 between the absorbent core 28 and the topsheet 24. The opening 70 may be at least partially maintained under pressure induced by the weight of the wearer. Nonlimiting, exemplary spacers 60 are disclosed in the aforementioned patents incorporated by reference above.

Alternatively, the spacer may define an opening providing a passageway between an aperture in an upper layer and a void space between the upper layer and an underlying layer.

Figure 3A:
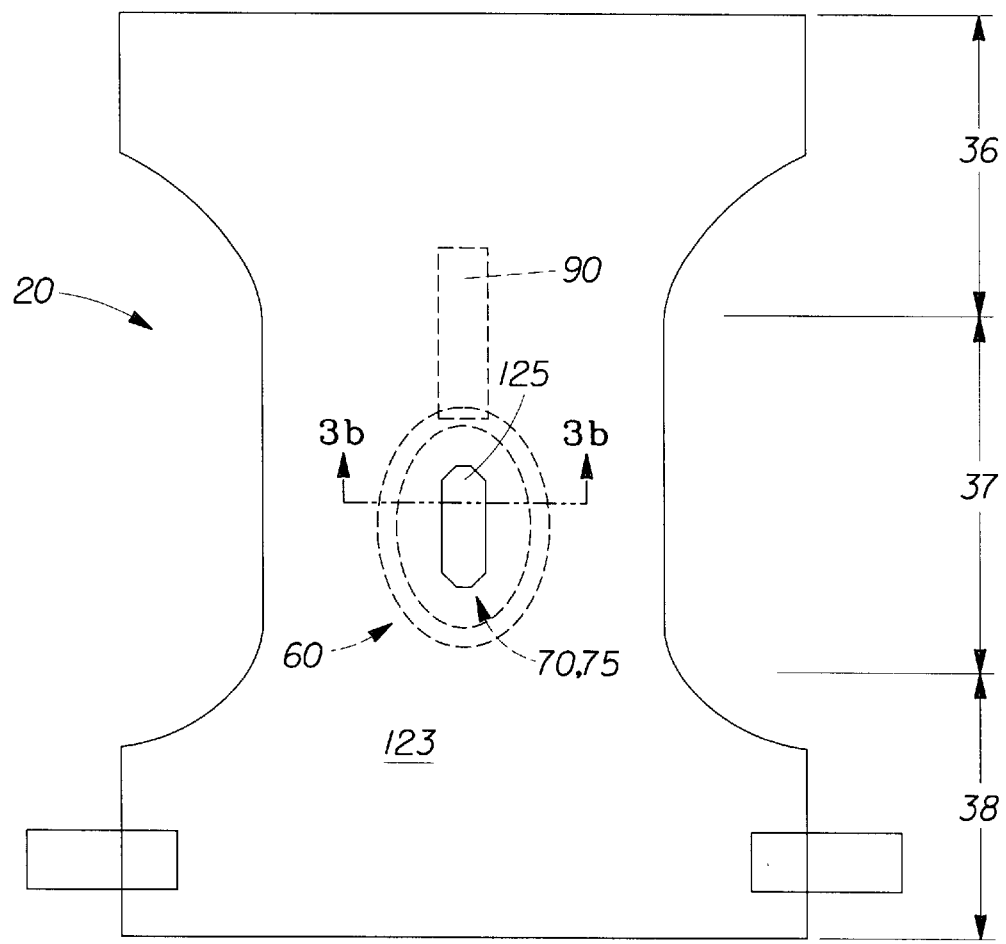
FIG. 3a is a plan view of a disposable diaper configuration of the present invention.
Figure 3B:
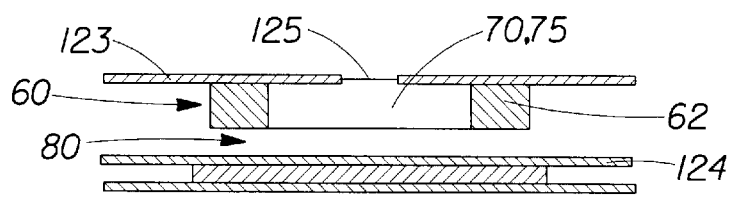
FIG. 3b is a cross-sectional view of the embodiment depicted in FIG. 3a showing the spacer opening providing a passageway to a primary void space.
Figure 3C:
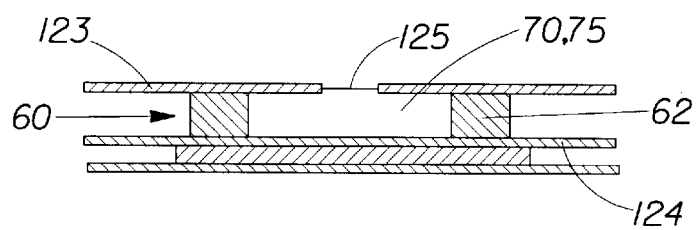
FIG. 3c is a cross-sectional view of the embodiment depicted in FIG. 3a showing the configuration of the spacer when the article is compressed under the weight of the wearer.

For example, the embodiment shown in FIGS. 3a and 3b, includes a secondary topsheet 123 covering a primary topsheet 124, disposed in a face-to-face arrangement therewith and joined thereto along the edges, creating a primary void space 80 for receiving bodily exudates therein. The primary void space 80 is in communication with an aperture 125 in the secondary topsheet 123. The spacer 60 is interposed between the primary and secondary topsheets 123, 124 with the opening 70 aligned with the aperture 125 to provide a passageway to the primary void space 80. The opening 70 may also provide a secondary void space capable of receiving bodily exudates. In one embodiment as shown in FIG. 3c, the secondary void space may be at least partially maintained by the body 62 of the spacer 60 even when the article is compressed by the weight of the wearer.

Figure 5A:
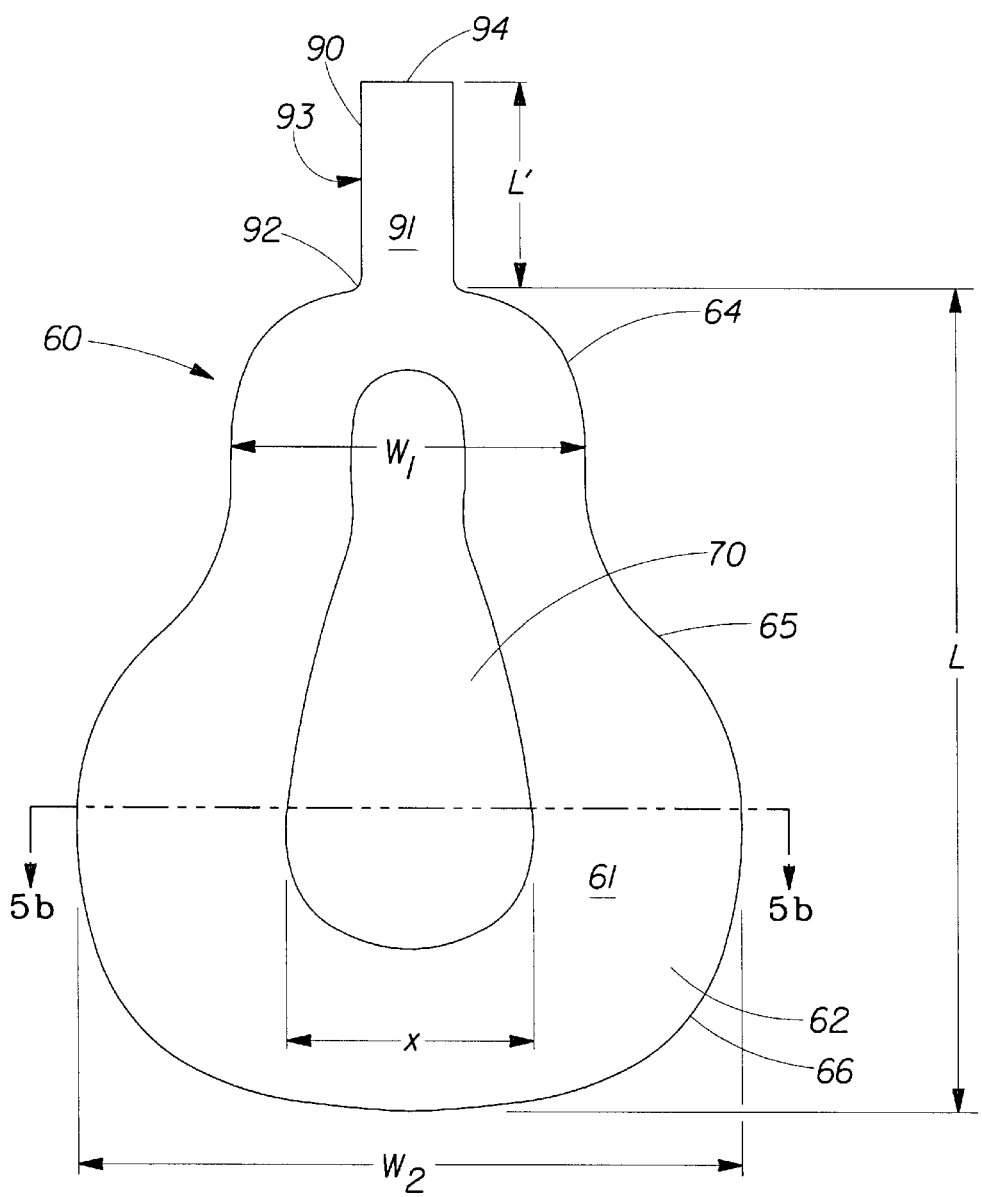
FIG. 5a is a plan view of a spacer suitable for use with the present invention.
Figure 5B:
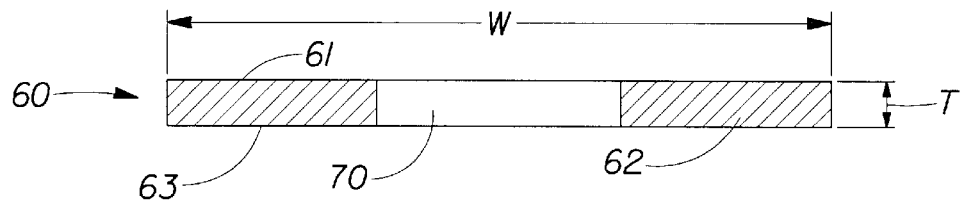

The spacer 60 may be of any suitable size and/ or shape. As shown in FIG. 5a, the spacer has a first end 64 and a second end 66 longitudinally opposite the first end 64 and a length L measured therebetween. In preferred embodiments, the spacer 60 has a topside 61 facing the body of the wearer, a bottom side 63 opposite the topside 61 and a thickness, T, measured between the topside and the bottom side as shown in FIG. 5b. The thickness, T, of the spacer 60 preferably ranges between about 0.5 cm and about 3.0 cm in use. The spacer 60 is preferably disposed in the crotch region 37 of the diaper 20 and oriented such that the first end 64 is located toward the first waist region 36 of the diaper 20 and the second end 66 is located toward the second waist region 38 of the diaper 20.

Whether the spacer 60 defines an opening 70 providing the void space (FIGS. 2a and 2b) or provides a portion of the void space while defining a passageway to the larger void space (primary void space 80 shown in FIGS. 3a and 3b), it is preferred that the volume of the opening 70 ranges between about 10 cubic cm and about 150 cubic cm, and preferably between about 25 cubic cm and about 75 cubic cm. It is also preferred that the lateral dimension X of the opening 70 be large enough to accommodate the feces, but narrow enough such that the spacer 60 can support the ischia of the wearer. Preferably, the lateral dimension X of the opening 70, defined by the spacer 60 in the area corresponding to the anus of the wearer, is between about 1 cm and about 5 cm, and more preferably between about 1.5 cm and about 3.5 cm.

Although the shape of the spacer 60 is not critical, "keyhole" shaped spacers (e.g. the spacer shown in FIG. 5a) and "elliptically shaped" spacers perform particularly well. As shown in FIG. 5a, it is preferred that the spacer 60 have a width, $W_1$, at the first end 64 which is narrower than a width, $W_2$, at the second end 66 in order to provide a smaller radius of curvature at the first end 64 which comfortably accommodates the thighs of the wearer. Even though the spacer 60 may be made according to any suitable size, for disposable diapers, the spacer 60 width, $W_1$, preferably ranges from about 0.5 cm to about 2.0 cm while the spacer width, $W_2$, preferably ranges from about 5.0 cm to about 8.0 cm.

Figure 4A:
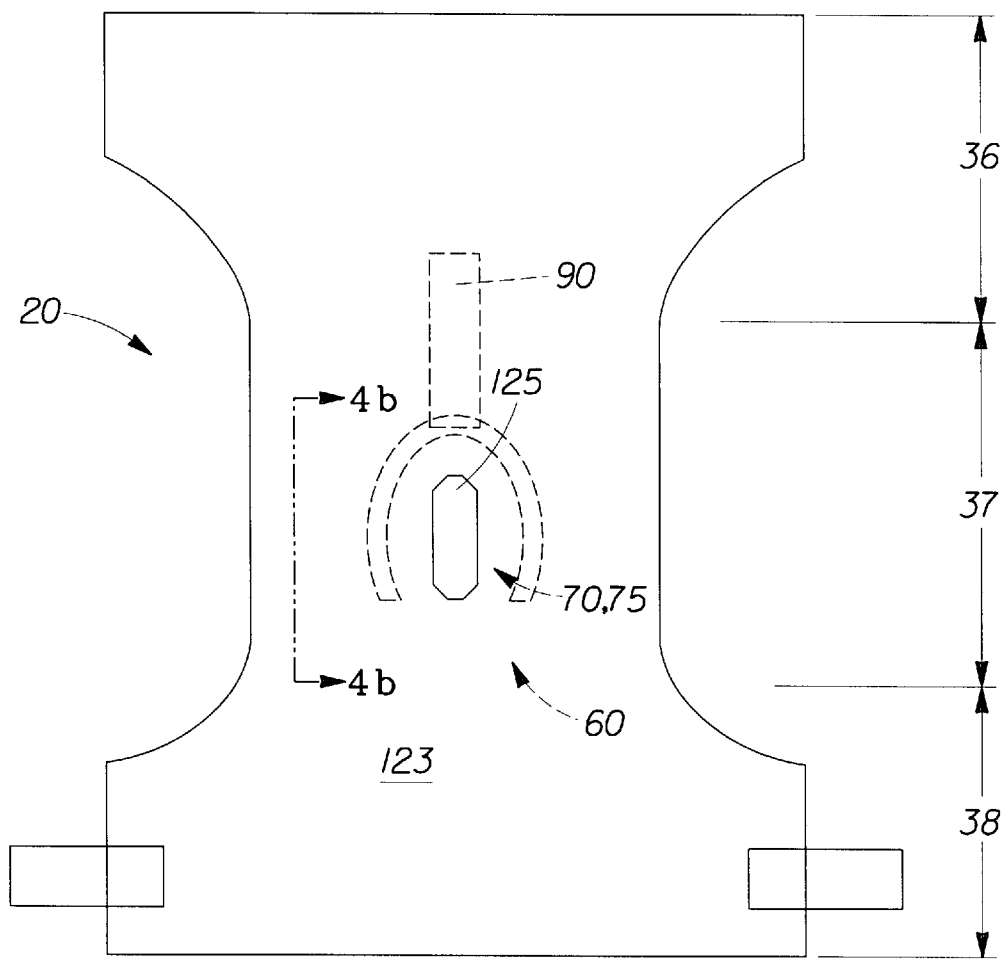
FIG. 4a is a plan view of a disposable diaper configuration of the present invention having an open ended spacer.
Figure 4B:
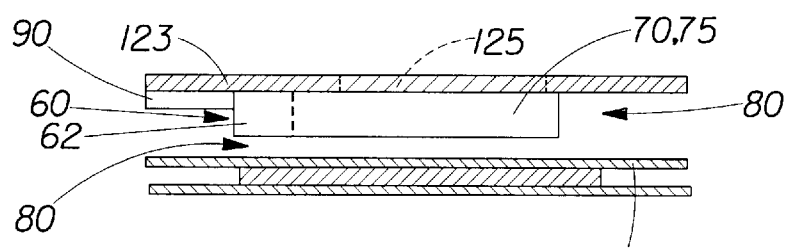
FIG. 4b is a cross-sectional view of the embodiment depicted in FIG. 4a showing the spacer opening providing a passageway to a primary void space.
Figure 4C:
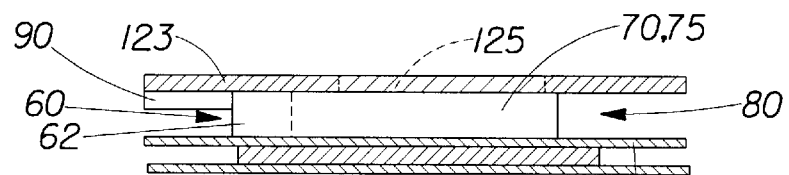
FIG. 4c is a cross-sectional view of the embodiment depicted in FIG. 4a showing the configuration of the spacer when the article is compressed under the weight of the wearer.

Alternatively, U-shaped (or other open ended) spacers may be suitable for use in certain embodiments (preferably with the open end of the spacer oriented toward the second waist region 38 of the diaper 20 as shown in FIG. 4a). For this embodiment, the opening 70 provides a passageway to the primary void space 80 as depicted in FIG. 4b. The opening 70 may also provide a secondary void space 75 capable of receiving bodily exudates. For this embodiment, a portion of the secondary void space 75 may be at least partially maintained by the body 62 of the spacer 60 even when the article is compressed by the weight of the wearer, as shown in FIG. 4c. In addition, since the spacer is open ended, the passageway to the primary void space 80 may also be at least partially maintained when the article is in the compressed state.

Nevertheless, the spacer 60 may be unitary or may comprise a multiplicity of separate or operatively associated parts. Further, the spacer 60 may have a closed perimeter 65 or may comprise openings, holes, or channels extending from the passageway 70 through the spacer body 62 to the perimeter 65 of the spacer 60. Such embodiments may be useful to allow distribution of feces from the opening 70 to another void space or other parts of the diaper 20.

The spacer 60 may comprise any material or combination of materials which are suitable for use in an absorbent article to be worn by a human wearer. For example, the spacer 60 may include foams, woven or nonwoven webs, thermoplastic materials, organic materials, fibers, gels, rubber or synthetic rubber, etc. In one embodiment, the spacer comprises an air filled bladder. In another embodiment, the spacer 60 comprises an absorbent foam made from a 16:1 water/oil emulsion, having a glass transition temperature of about 10° C., and having a compression of about 40% in a dry state and about 30% in a wet state (i.e., when saturated with water) under about 1.0 psi applied pressure. Thus, in certain embodiments, the compression under about 1.0 psi in the wet state may be less than the compression under about 1 psi in the dry state. A suitable foam includes high internal phase emulsions as disclosed in U.S. Pat. No. 5,625,222 entitled "Absorbent Foam Materials For Aqueous Fluids Made From High Internal Phase Emulsions Having Very High Water-To-Oil Ratios" issued to DesMarais et al. on Jul. 22, 1997, the disclosure of which is incorporated herein by reference.

In a preferred embodiment, the spacer 60 is relatively soft, but resilient and capable of withstanding the forces typical of a baby's movements and/or the weight of a baby sitting or lying on the spacer 60. Thus, the spacer 60 should be capable of withstanding at least 0.5 psi and preferably at least about 1.0 psi while compressing no more than about 60%, and preferably no more than about 30% in both wet and dry conditions.

In yet another embodiment, the spacer 60 may be activatable during use. That is, the spacer 60 may be stored in the diaper 20 in one configuration and may be activated by some event or material which changes the configuration of the spacer 60 or the surrounding structure so as to provide the diaper 20 with a desired configuration for receiving and/or storing bodily exudates. For example, the spacer 60 may include a material which expands when contacted by water, urine, feces, enzymes or other means associated with the wearer's body or bodily exudates. Changes in temperature, pH and saline concentration are also "triggers" which can activate the spacer 60. Thus, when the wearer urinates, the spacer 60 may increase in thickness, change shape or otherwise orient itself in the diaper 20 to provide a passageway 70 into which urine and/or feces can flow.

The advantages of a diaper including an apertured topsheet and a spacer 60 are significantly reduced if the aperture in the topsheet and the opening 70 provided by the spacer 60 do not stay aligned with the point of discharge (i.e. wearer's anus) throughout the time of use (or at least until the wearer has a bowel movement). Accordingly, the diaper 20 of the present invention includes a means for maintaining the spacer opening 70 in alignment with the aperture and the wearer's anus. Preferably, the diaper 20 includes an alignment guide 90 that is operatively connected to the spacer 60. By "operatively connected" it is meant that the alignment guide can be joined to the spacer (adhesively or via a fastener such as thread, string etc.) or integral with the spacer as an extension thereof.

In the configuration depicted in FIG. 5a, the alignment guide 90 includes a first end edge 92, a second end edge 94 longitudinally opposite the first end edge 92 with an elongate portion having a length, L' therebetween, a topside 91 and a bottom side 93. Like the spacer 60, the alignment guide 90 may be disposed between the topsheet 24 and the absorbent core 28 and/or other underlying layers such as sublayers, acquisition layers and the like. For the embodiment shown in FIG. 5a, the first end edge 92 is integral with the first end 64 of the spacer 60 while the second end edge 94 of the alignment guide 90 is cantilevered from the spacer 60. For the embodiments shown in FIGS. 2a and 3a, the second end edge 94 of the alignment guide 90 extends forward from the spacer 60 into the first waist region 36 toward the front waist of the diaper 20. The alignment guide 90 is preferably long enough so that the second end edge 94 extends between a wearer's legs when the diaper 20 is worn. This results in the spacer 60 being held in the correct longitudinal and lateral position on the diaper 20 and in the correct Z-direction orientation to the point of discharge on the wearer (eg. wearer's anus) to facilitate receiving feces. The alignment guide 90 is preferably sized so that the ratio of the alignment guide length, L', to the spacer length, L, ranges from about 0.1 to about 5.0, more preferably from about 0.5 to about 2.0.

The alignment guide 90 can be made of the same material as the spacer 60, particularly where the alignment guide 90 is integral with the spacer 60, or can be made of material which is distinct from the spacer material. The alignment guide 90 may be inelastic and include stiff materials such as foam or cardboard, thermoplastic materials, or organic materials or else may be elastic and include flexible materials such as woven or nonwoven webs, fibers, gels, rubber or synthetic rubber, paper etc. Further, the alignment guide 90 may be unitary or may comprise a multiplicity of separate or operatively associated parts.

Figure 6:
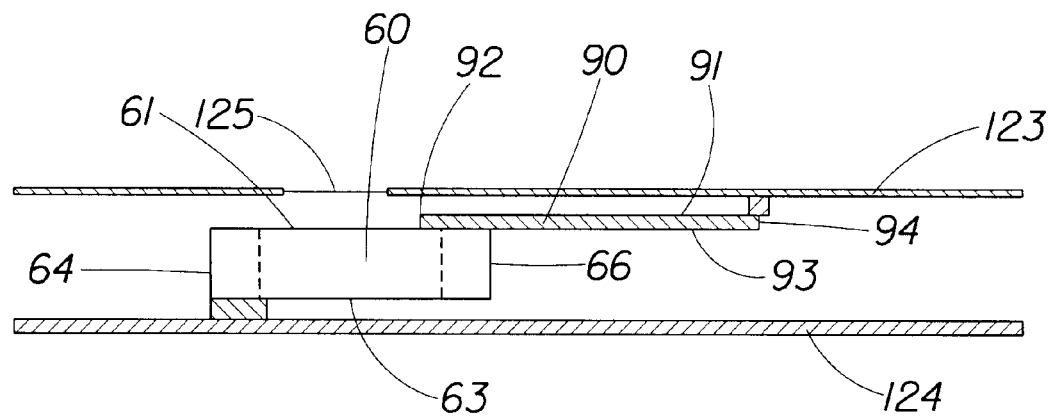
FIG. 6 is a cross-sectional view of a spacer and alignment guide configuration illustrating the locations where the spacer/alignment guide configuration is joined to the absorbent article.

The spacer 60/alignment guide 90 combination may be joined to the absorbent article in a number of different arrangements in order to keep the spacer opening 70 aligned with the point of discharge on the wearer (e.g. wearer's anus). Preferably, the bottom side 63 of the spacer near the first end 64 may be joined with at least a portion of the layer which underlies the spacer 60, such as the core 28, a primary topsheet 124 (FIGS. 3a and 3b), a sublayer or the backsheet 28, and at least a portion of the second end edge 94 of the alignment guide 90 may be joined to either the same underlying layer as the spacer 60 or an upper layer. However, more preferably as shown in FIG. 6, at least a portion of the second end edge 94 of the alignment guide 90 is joined to an upper layer such as a secondary topsheet 123 while a portion of the bottom side 63 of the spacer 60 near the first end 64 is joined to an underlying layer. Further, FIG. 6 shows a portion of the topside 91 of the alignment guide near the second end edge may be joined to an upper layer such as a secondary topsheet 123 while a portion of the bottom side 63 of the spacer 60 near the first end 64 may be joined to the underlying layer such as a primary topsheet 124. Nonetheless, the spacer 60 may be joined directly or indirectly by any means known in the art. Typical joining means include adhesives, heat, pressure, static, magnetism, snaps, hook and loop fasteners and the like.

Figure 7:
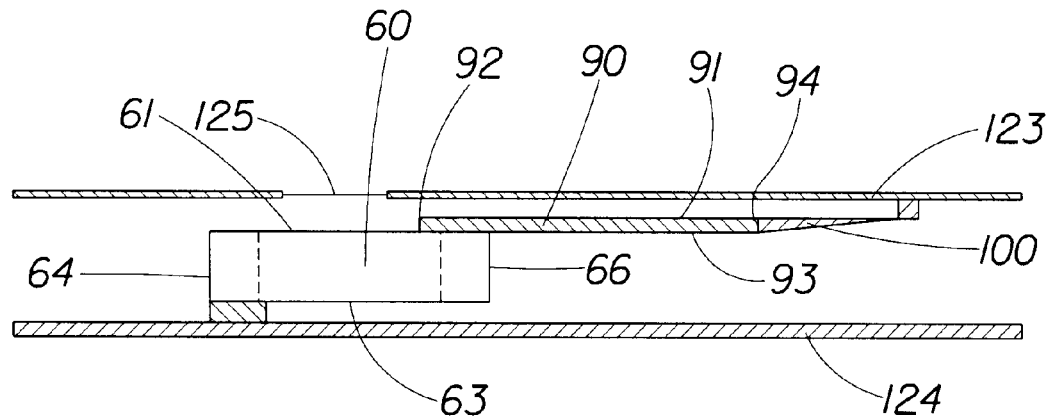
FIG. 7 is a cross-sectional view of a spacer and alignment guide configuration including an extension element attached to the end of the alignment guide.

In an alternate embodiment, the alignment guide comprises at least two different materials having distinct physical properties. For instance, the alignment guide 90 shown in FIG. 7 includes an extension element 100 joined to the second end edge 94. The extension element 100 is preferably elastic and is particularly suitable for embodiments incorporating inelastic alignment guides in order to facilitate and maintain attachment to the article. Stiff inelastic alignment guides may break or pull away from a point of attachment as a result of forces induced by an active wearer. For this embodiment the extension element 100 is joined to either the secondary topsheet 123, underlying layer or both as previously described.

In one embodiment, the diaper 20 includes a topical adhesive or body adhering composition which acts to hold an aperture in the topsheet in place during use. The topical adhesive may be located on the topsheet 24. However, the body adhering composition may also be integral with the material making up the topsheet 24 or other element of the absorbent article or may be a separate material disposed directly or indirectly on all or any portion of the absorbent article. Further, the body adhering composition may be disposed on any portion of the absorbent article in any pattern or configuration including, but not limited to lines, stripes, dots, and the like.

In one preferred embodiment shown in FIG. 2a, the topical adhesive 50 is disposed on the topsheet 24 in a continuous ring about the aperture 25. However, embodiments are contemplated wherein the topical adhesive 50 surrounds only a portion of the aperture 25 and/or is disposed in locations not directly adjacent the aperture 25, such as around the edge of the topsheet 24, on the leg cuffs 32 or in one or both of the waist regions. Alternatively, topical adhesive 50 may be disposed on the spacer 60 itself. If this is done, the topical adhesive 50 may be on an exposed surface of the spacer 60 or may be located beneath an apertured, slit or otherwise reticulated layer such that the topical adhesive 50 can contact the wearer in use.

Types of body adhering composition may include any one or more substances capable of releasably adhering to the skin of the wearer. Further, the body adhering composition may be in the form of a gel, lotion, film, web or the like. Examples of suitable body adhering compositions include adhesives, gelatin, petrolatum, waxes such as silicone or petroleum waxes, oils such as silicone or petroleum based oils, skin care compositions or ingredients thereof, as described below, and the like. Suitable topical adhesives include, but are not limited to, hydrogel or hydrocolloid adhesives such as acrylic based polymeric adhesives, and the like. (Some exemplary hydrogel and/or hydrocolloid adhesives are disclosed in U.S. Pat. Nos. 4,231,369; 4,593,053; 4,699,146; 4,738,257; and 5,726,250; each of which is incorporated by reference herein.) The topical adhesives may also include any "medical adhesives" which is compatible for use with biological tissue, such as skin. Acrylic medical adhesives suitable for use as body adhering compositions, include adhesives available from Adhesive Research, Inc., of Glen Rock, PA, under the designations MA-46, MA-312, "MTTM" High MVTR adhesive, and AS-17. Rubber-based medical adhesives, such as SB-2 from Adhesive Research Inc. may also be suitable. Other exemplary adhesives include Dow Corning Medical Adhesive (Type B) available from Dow Corning, Midland, MI; "MEDICAL ADHESIVE" from Hollister Inc., of Libertyville, IL; 3M Spray Adhesives #79, 76, 77 and 90 available from the 3M Corp. of St. Paul, MN; and "MATI-SOL" liquid adhesive available from Ferndale Laboratories of Ferndale, MI. Other medical adhesives are described in U.S. Pat. Nos. 4,078,568; 4,140,115; 4,192,785; 4,393,080; 4,505,976; 4,551,490; 4,768,503 and polyacrylate and polymethacrylate hydrogel adhesives are disclosed in U.S. Pat. Nos. 5,614,586 and 5,674,275; the disclosure of each of which is incorporated by reference herein. Yet another exemplary adhesive comprising polyvinyl pyrollidone and a multi-functional amine-containing polymer is disclosed in WO 94/13235A1. (The disclosure of each of these references is incorporated herein by reference.) Alternative body adhering means which may be used in place of or in addition to those described above include static electricity, suction and the like. In any case, it is preferred that the body adhering composition permit vapors to pass (i.e., breathable), be compatible with the skin and otherwise skin friendly. Further, it is preferred that the body adhesive be at least partially hydrophobic, preferably 60%, more preferably 80%, by weight of the adhesive consist of hydrophobic components. However, hydrophilic adhesives are contemplated in certain embodiments of the present invention.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A wearable article including a spacer and a primary void space for receiving bodily exudates therein, the spacer comprising:
   a body having an opening therein providing a passageway to the primary void space, wherein a portion of the opening is maintained when the article is subjected to compressive loading to provide a secondary void space for receiving bodily exudates therein, and
   an alignment guide for maintaining the spacer opening in alignment with a point of discharge on the wearer when the wearable article is worn,
   the wearable article further comprising at least two layers and the spacer disposed intermediate the at least two layers, and
   wherein the spacer further comprises a first end and a second end opposite the first end, and wherein the alignment guide comprises a first end edge and a second end edge opposite the first end edge, a portion of the spacer near the second end is joined to one of the layers of the article, the first end edge of the alignment guide is joined to the first end of the spacer, and the second end edge of the alignment guide is joined to one of the layers.

2. The wearable article as defined in claim 1 wherein the spacer comprises an air filled bladder.

3. A wearable article as defined in claim 1 wherein the alignment guide further comprises a length and wherein a ratio of the alignment guide length to the spacer length ranges from about 0.1 to about 5.

4. A wearable article as defined in claim 1 wherein the alignment guide comprises a separate element joined to the spacer.

5. A wearable article as defined in claim 1 wherein the alignment guide comprises at least two different materials having different physical properties.

6. A wearable article including a spacer and a primary void space for receiving bodily exudates therein, the spacer comprising:
   a body having an opening therein providing a passageway to the primary void space, wherein a portion of the opening is maintained when the article is subjected to compressive loading to provide a secondary void space for receiving bodily exudates therein, and an alignment guide for maintaining the spacer opening in alignment with a point of discharge on the wearer when the wearable article is worn, the wearable article further comprising:
a backsheet;
a topsheet joined to the backsheet to form the primary void space, the topsheet having an aperture disposed therein in communication with the primary void space; and
an absorbent core disposed intermediate the backsheet and the topsheet,
wherein the spacer is disposed intermediate the topsheet and the absorbent core such that the opening is in register with the aperture, and
wherein the spacer further comprises a first end and a second end opposite the first end and wherein the alignment guide comprises a first end edge and a second end edge opposite the first end edge; a portion of the spacer near the second end is joined to an underlying layer while the first end of the spacer is joined to the first end edge of the alignment guide; the second end edge of the alignment guide is joined to the topsheet.

7. A disposable diaper having a first waist region, a second waist region, and a crotch region interposed therebetween, the disposable diaper comprising:
a backsheet;
a primary topsheet joined to the backsheet;
an absorbent core disposed intermediate the backsheet and the primary topsheet;

a secondary topsheet covering at least a portion of the primary topsheet and joined thereto to form a primary void space for receiving fecal matter therein, the secondary topsheet having an aperture disposed therein in communication with the primary void space;

a spacer disposed in the crotch region for maintaining a Z direction separation between the primary topsheet and the secondary topsheet, the spacer comprising a body having an opening therein providing a passageway to the primary void space wherein at least a portion of the opening is maintained when the article is subjected to compressive loading to provide a secondary void space for receiving fecal matter therein; and an alignment guide for maintaining the spacer opening in alignment with a wearer's anus when the disposable diaper is worn.

8. A disposable diaper as defined in claim 7 wherein a portion of the passageway to the primary void space is maintained when the article is subjected to compressive loading.

9. A disposable diaper as defined in claim 7 wherein the spacer further comprises a first end and a second end opposite the first end, and wherein the alignment guide comprises a first end edge and a second end edge opposite the first end edge, a portion of the spacer near the second end is joined to the primary topsheet while the first end of the spacer is joined to the first end edge of the alignment guide; the second end edge of the alignment guide is joined to the secondary topsheet.

10. The disposable diaper as defined in claim 7 wherein the secondary topsheet comprises a topical adhesive disposed around a portion of the aperture.

* * * * *

UNITED STATES PATENT AND TRADEMARK OFFICE
CERTIFICATE OF CORRECTION

PATENT NO. : 6,595,972 B1
DATED : July 22, 2003
INVENTOR(S) : Brandon E. Wise et al.

It is certified that error appears in the above-identified patent and that said Letters Patent is hereby corrected as shown below:

Column 9,
Line 51, delete "adhesives" amd insert -- adhesive --.

Signed and Sealed this

Twentieth Day of July, 2004

JON W. DUDAS
*Acting Director of the United States Patent and Trademark Office*